(12) United States Patent
Framroze

(10) Patent No.: US 7,002,008 B2
(45) Date of Patent: Feb. 21, 2006

(54) PROCESS FOR THE PREPARATION OF 1-(4-FLUOROPHENYL)-4(S)-(4-HYDROXYPHENYL)-AZETIDIN-2-ONE

(76) Inventor: Bomi Patel Framroze, Shree Sadan, 4/A Carmichael Rd., Mumbai (IN) 400026

( * ) Notice: Subject to any disclaimer, the term of this patent is extended or adjusted under 35 U.S.C. 154(b) by 272 days.

(21) Appl. No.: 10/460,877

(22) Filed: Jun. 16, 2003

(65) Prior Publication Data

US 2004/0254369 A1    Dec. 16, 2004

(51) Int. Cl.
*C07D 205/08*    (2006.01)
*C07C 309/66*    (2006.01)
*C07C 303/28*    (2006.01)

(52) U.S. Cl. ......................................... 540/200; 558/52
(58) Field of Classification Search ................... 558/52; 540/200
See application file for complete search history.

(56) References Cited

U.S. PATENT DOCUMENTS 5,856,473 A * 1/1999 Shankar ...................... 540/200
6,207,822 B1 * 3/2001 Thiruvengadam et al. .. 540/200

* cited by examiner

*Primary Examiner*—Mark L. Berch
(74) *Attorney, Agent, or Firm*—David M. Gange

(57) ABSTRACT

A process for preparing a compound of the formula

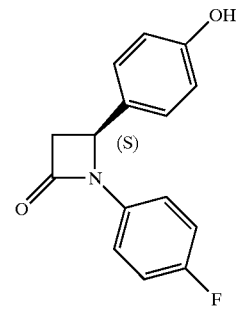

comprising:
(a) formation of 3(S)-(4-hydroxyphenyl)-3-methanesulfonyloxy-propionic acid methyl ester compound of the formula

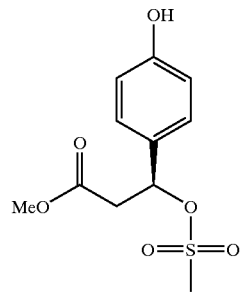

(b) cyclization of the product of Step (a) with 4-fluoroaniline to yield 1-(4-fluorophenyl)-4(S)-(4-hydroxyphenyl)-azetidin-2-one.

11 Claims, No Drawings

PROCESS FOR THE PREPARATION OF 1-(4-FLUOROPHENYL)-4(S)-(4-HYDROXYPHENYL)-AZETIDIN-2-ONE

CROSS REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

REFERENCES CITED

U.S. Patent Documents

| | | |
|---|---|---|
| 5,856,473 | January 1999 | Banderpalle |
| 5,886,171 | March 1999 | Wu |
| 6,133,001 | October 2000 | Homann |
| 6,207,882 | March 2001 | Ding |

Foreign Patent Documents

| | | |
|---|---|---|
| WO95/08532 | March 1995 | WIPO |
| WO93/02048 | February 1993 | WIPO |
| WO97/45406 | December 1997 | WIPO |
| WO97/16424 | May 1997 | WIPO |

Other Documents
La Manna et al., Farmaco Ed. Sci. Vol 19, pg.506, (1964)

BACKGROUND

Process for the preparation of 1-(4-fluorophenyl)-4(S)-(4-hydroxyphenyl)-azetidin-2-one.

This invention relates to a process for preparing 1-(4-fluorophenyl)-4(S)-(4-hydroxyphenyl)-azetidin-2-one, a compound useful as an intermediate in the preparation of hypocholesterolemic agents, and to the preparation of 3(R)-(4-hydroxy-phenyl)-3-methanesulfonyloxy propionic acid methyl ester, a novel intermediate in the above mentioned process.

WO 95/08532 discloses a series of hypocholesterolemic agents comprising 3-hydroxypropyl azetidinones and describes several processes suitable for preparing these azetidinones. WO 93/02048 discloses a process to stereoselectively prepare 3- and 4-substituted azetidinones by cyclization of beta-amino amides. WO 95/08532 and WO 97/45406 disclose a method to prepare 3- and 4-substituted azetidinones by reacting 4-phenylbutyrolactones and 4-methoxybenzylideneaniline. WO97/16424 discloses a method to prepare the desired 3- and 4-substituted azetidinones by reacting 4-fluorocinnamyl bromide and a lactam.

More recently U.S. Pat. No. 6,207,882 describes a process to generate 3- and 4-substituted azetidinones streoselectively using p-fluorobenzoylbutyric acid and chiral 4-phenyloxazolidon-2-ones. U.S. Pat. No. 5,886,171 had also previously described a stereoselective process to the desired azetidinones starting from 3(S)-hydroxy-gamma-lactone. U.S. Pat. No. 6,133,001 describes an enzymatic microbial reduction of a 3-keto azetidinone. Other methods exist in the prior art which teach the process of converting the 3-unsubstituted azetidinone, which is the subject of this patent, into 3-, 4-substituted azetidinone hypocholesterolemic agents, such as by the method described in U.S. Pat. No. 5,856,473.

SUMMARY OF THE INVENTION

This invention provides a novel process for preparing a compound of the formula I

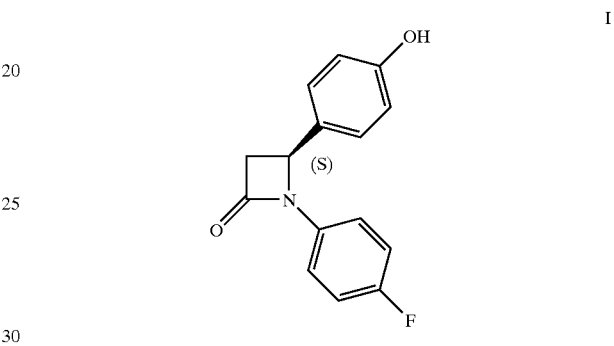

comprising:
(a) resolving the racemic propionic acid of formula II, making its methyl ester and forming its mesylate using methane sulfonyl chloride to give a compound of formula III

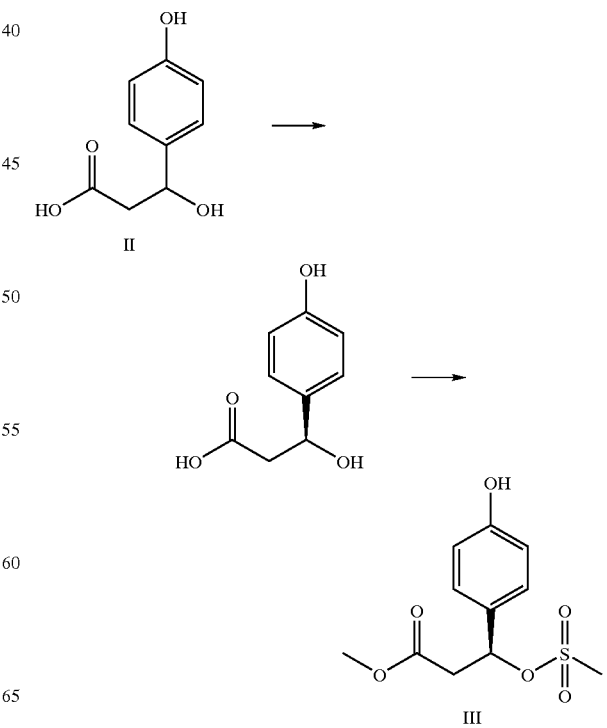

(b) reacting the compound of formula III with 4-fluoro aniline to give the desired azetidinone compound of formula I The invention also relates more particularly to step (b), wherein the compound of formula III is cyclized, in the presence of sodium iodide, with 4-fluoroaniline to yield the azetidinone compound of formula I.

The process described herein in this invention is a novel method to stereospecifically generate 4-substituted azetidinones, compared to the procedures described in the prior art. More specifically, the process of this invention, compared to the procedures for preparing the compound of formula I disclosed in the prior art, is a simpler procedure, involving mild reagents and starting materials, which are commonly available in commercial accessible quantities and having an improved overall yield. The compound of formula I is produced with greater efficiency in a highly stereoselective manner.

DETAILED DESCRIPTION

In step (a) of the process, the racemic 3-(4-hydroxyphenyl)-3-hydroxy-propionic acid of formula II (La Manna, Farmaco Ed. Sci. Vol. 19, Pg. 506, 1964) is resolved using (+)-2-amino-1-butanol and esterified with acidic methanol to give the resolved 3(S)-(4-hydroxyphenyl)-3-hydroxy-propionic acid methyl ester. The methyl ester and is further reacted with 1 equivalent of methane sulfonyl chloride at −10 degrees C., to selectively mesylate the primary hydroxy group in the presence of the aromatic hydroxy group, to obtain a compound of formula III.

In step (b), the compound of formula III and 1 equivalent of 4-fluoroaniline is dissolved in acetone, or any other suitable protic polar solvent, and 1% to 10% mol/mol of sodium iodide or other alkali halide is added to the solution at room temperature and the mixture refluxed until the reaction is complete, to obtain the desired azetidinone compound of formula I.

The compound of formula III is unknown in the prior art and is claimed herein as a key intermediate in this novel process to azetidinone compounds which are key intermediates to hypocholesterolemic azetidinone agents known in the art.

Following are examples of the claimed process.

EXAMPLE 1

To 14.6 gm of compound of formula II and 8 gm of (+)-2-amino-2-butanol was added 150 ml of 2:1 solution of ethanol and water near its boiling point until dissolution just occurs. After cooling, the preciptated salt was collected and dried to yield 13.1 gm of 3(S)-(4-hydroxyphenyl)-3-hydroxy-propionic acid butanol amine salt with >92% ee (enantiomeric excess). The salt was added to a solution of 400 ml of 5% hydrochloric acid in methanol and refluxed for 2 hours and the methanol evaporated under vacuum. 200 ml of methylene chloride and 200 ml of water was added to the residue and the layers separated. the organic layer was evaporated to yield 12.9 gm of 3(S)-(4-hydroxyphenyl)-3-hydroxy-propionic methyl ester which was dissolved in 100 ml of THF and to it was added 9.2 gm of methane sulfonyl chloride and 28 ml of triethylamine. the solution was allowed to stir at 35 degrees C. for 2 hours, cooled and evaporated to near dryness. To this residue was added 100 ml of methylene chloride and 100 ml of water and the layers separated. The organic layer was washed with 1N hydrochloric acid and saturated sodium bicarbonate, separated, dried over sodium sulfate and evaporated to yield 14.1 gm of a compound of formula III.

¹H NMR-δ7.56, d, 2H; δ7.36, d, 2H; δ4.21, dd, 1H; δ3.61, s, 3H; δ3.34, s, 3H; δ2.01, t, 2H.

EXAMPLE 2

To 25.9 gm of the compound of formula III dissolved in 250 ml of acetone was added 11.1 gm of 4-fluoroaniline and 7 gm of sodium iodine. The mixture was refluxed for 8 hours and the acetone was removed under vacuum. The residue was added 200 ml of ethyl ester and washed with saturated sodium bicarbonate, water, separated and evaporated to yield 22.4 gm of the azetidinone of formula I.

¹H NMR-δ7.69, d, 2H; δ7.56, d, 2H; δ7.38, d, 2H; δ7.27, d, 2H; δ3.62, dd, 1H; δ2.14, t, 2H.

I claim:

1. A compound of formula III and

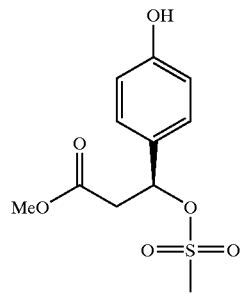

chemical name 3(S)-(4-hydroxyphenyl)-3-methanesulfonyloxy-propionic acid methyl ester.

2. A process for preparing a compound of formula I comprising:

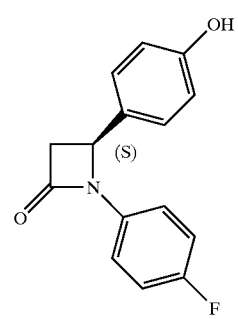

(a) resolving racemic 3-(4-hydroxyphenyl)-3-hydroxy-propionic acid into 3(R)-(4-hydroxyphenyl)-3-hydroxy-propionic acid and 3(S)-(4-hydroxyphenyl)-3-hydroxy-propionic acid;

(b) making 3(S)-(4-hydroxyphenyl)-3-hydroxy-propionic acid methyl ester from 3(S)-(4-hydroxyphenyl)-3-hydroxy-propionic acid;

(c) forming 3(S)-(4-hydroxyphenyl)-3-methanesulfonyloxy-propionic acid methyl ester by contacting 3(S)-(4-hydroxyphenyl)-3-hydroxy-propionic acid methyl ester with methane sulfonyl chloride;

(d) reacting 3(S)-(4-hydroxyphenyl)-3-methanesulfonyloxy-propionic acid methyl ester with 4-fluoroaniline in the presence of alkali halide to form the compound of formula I.

3. The process of claim 2 wherein step (a) comprises contacting 3-(4-hydroxyphenyl)-3-hydroxy-propionic acid with (+)-2-amino-1-butanol.

4. The process of claim 2 wherein the methyl ester is made by adding 3(S)-(4-hydroxyphenyl)-3-hydroxy-propionic acid to a solution comprising acidic methanol.

5. The process of claim 4 wherein the acidic methanol comprises about 5% hydrochloric acid in methanol.

6. The process of claim 2 wherein the methyl ester is made by adding the salt of 3(S)-(4-hydroxyphenyl)-3-hydroxy-propionic acid with (+)2-amino-1-butanol to a solution comprising acidic methanol.

7. The process of claim 6 wherein the acidic methanol comprises about 5% hydrochloric acid in methanol.

8. The process of claim 2 wherein step (c) of the process is carried out at about −10 degrees C.

9. The process of claim 2 wherein step (c) of the process is carried out at about 35 degrees C.

10. The process of claim 2 wherein the alkali halide comprises sodium iodide.

11. The process of claim 2 wherein the concentration of alkali halide is between about 1 mol % to about 10 mol %.

* * * * *